United States Patent [19]

Salo

[11] Patent Number: 5,312,452
[45] Date of Patent: May 17, 1994

[54] CARDIAC RHYTHM MANAGEMENT DEVICE WITH AUTOMATIC OPTIMIZATION OF PERFORMANCE RELATED PACING PARAMETERS

[75] Inventor: Rodney W. Salo, Fridley, Minn.

[73] Assignee: Cardiac Pacemakers, Inc., St. Paul, Minn.

[21] Appl. No.: 970,892

[22] Filed: Nov. 3, 1992

[51] Int. Cl.$^5$ ............................................. A61N 1/00
[52] U.S. Cl. ..................................................... 607/17
[58] Field of Search ...................................... 607/11–13, 607/25–28, 64, 14, 17, 19; 128/703, 706

[56] References Cited

U.S. PATENT DOCUMENTS

| | | | |
|---|---|---|---|
| 3,902,479 | 9/1975 | Chaumet | 128/703 |
| 4,592,367 | 6/1986 | Imran | 128/703 |
| 4,719,921 | 1/1988 | Chirife | 128/703 |
| 4,759,366 | 7/1988 | Callaghan | 607/13 |
| 4,759,367 | 7/1988 | Callaghan | 607/26 |

Primary Examiner—Lee S. Cohen
Assistant Examiner—Marianne Parker
Attorney, Agent, or Firm—Haugen and Nikolai

[57] ABSTRACT

A dual chamber cardiac pacemaker incorporating a microprocessor-based controller which is programmed to automatically establish an A-V interval at a value which provides optimum cardiac function but without the need for a special sensor for measuring cardiac function is described. The microprocessor is programmed to continuously monitor heart rate and variation in heart rate and only when the patient is stable, enter a parameter adjustment loop in which the pacemaker's A-V interval is incremented in several discrete steps and for each step, the corresponding average steady-state heart rate is measured and stored. When the A-V interval incrementation process causes that interval to reach a predetermined upper limit, the pacemaker's A-V interval is set at the value that corresponds with the minimum average heart rate to thereby maximize cardiac performance.

6 Claims, 2 Drawing Sheets

CARDIAC RHYTHM MANAGEMENT DEVICE WITH AUTOMATIC OPTIMIZATION OF PERFORMANCE RELATED PACING PARAMETERS

This application is a companion to application Ser. No. 07/970,893, filed Nov. 3, 1992, entitled "CARDIAC STIMULATING APPARATUS AND METHOD FOR HEART FAILURE THERAPY", filed concurrently herewith.

BACKGROUND OF THE INVENTION

I. Cross Reference to Related Applications

II. Field of the Invention

This invention relates generally to an improved cardiac rhythm management apparatus, and more particularly to an implantable cardiac stimulating device incorporating means for optimizing the A-V interval or other pacing parameters without the need for an additional sensor.

III. Discussion of the Prior Art

In the "Discussion of the Prior Art" section of the above-identified companion application, there is set out at length a discussion as to how the prior art in the field of implantable cardiac stimulating devices has not addressed a closed-loop adaptive system for adjusting the A-V interval between the occurrence of an atrial depolarization signal (natural or paced) and the generation of a succeeding ventricular stimulating pulse in such a way that the heart's cardiac function is optimized, especially in treating patients suffering from congestive heart failure (CHF). In accordance with the teachings of that application, a patient suffering from CHF has implanted in his/her body a cardiac stimulator and lead arrangement which allows for the sensing of atrial and ventricular activity along with a variable frequency pulse generator for stimulating at least one ventricular chamber, that pulse generator being controlled by a microprogrammable controller. In addition to the usual lead assembly used conventionally for sensing atrial and ventricular depolarization signals, a further sensor is utilized for measuring cardiac function and providing information relative thereto to the microprogrammable controller. That controller then operates to adjust the A-V interval in incremental steps until reaching a predetermined A-V delay limit value. For each of the incremental steps, the cardiac function sensor allows the system to determine whether a given incremental change in the A-V interval results in improved cardiac function. Ultimately, the A-V interval is set to the greatest length which is less than or equal to the limit value that yields maximal cardiac function.

The present invention differs from the device described in the aforereferenced companion application in that it obviates the need for an additional sensor, i.e., the sensor used to assess cardiac function.

Those skilled in the art will appreciate that the body has several mechanisms designed to adjust to metabolic demand by modifying cardiac output and, ultimately, oxygenation of tissue. The cardiac output may be increased or decreased by adjustment in sinus rate or stroke volume. Recognizing this fact, it should be possible to monitor metabolic demand by monitoring the sinus rate or the stroke volume or both. The present invention takes advantage of these mechanisms to optimize cardiac function in paced patients.

In a situation where the pacing rate is under sinus control, for example, in VDD pacing, any modification in a pacing parameter which decreases cardiac performance (and thus cardiac output) will, after a period of adjustment, result in an increased heart rate to regain the original cardiac output. Conversely, any change which improves cardiac performance will result in a decreased heart rate. Thus, the minimum, steady-state heart rate achieved following an incremental adjustment of a performance related pacing parameter, e.g., atrial-ventricular interval, will correspond to the optimum value of that parameter. It is, therefore, possible to optimize these parameters simply by monitoring the heart rate during the adjustment process, noting the value at which the minimum sinus rate occurs and setting the pacemaker to this parameter value at the conclusion of the procedure.

Before the above approach can be used to effect optimization of cardiac function, it is necessary to guarantee that the patient is in a stable hemodynamic condition at the time that heart rate is being measured following an incremental adjustment in the A-V interval. If the underlying condition is changing during the adjustment procedure, such as when the patient is exercising or under emotional stress, the heart rate will no longer be simply related to changes in the parameter being optimized and there can be no guarantee that the optimization procedure will converge to the correct value.

It is accordingly an object of the invention to provide an apparatus and method for optimizing cardiac function utilizing a cardiac stimulator that does not require a further sensor over and above the conventional sensing and stimulating electrodes on a conventional pacing lead.

Another object of the invention is to provide a method and apparatus for optimizing cardiac function in a patient suffering from cardiac disfunction, such as CHF, by setting the A-V delay interval of the implantable stimulating device to a value which corresponds to the lowest heart rate obtained during a series of measurements taken over a predetermined period of time and at times when the patient is found to be in a stable hemodynamic condition.

SUMMARY OF THE INVENTION

The foregoing features, objects and advantages of the invention are achieved in accordance herewith by providing a cardiac rhythm management device which comprises a means for sensing both atrial and ventricular depolarization signals and a variable frequency pulse generator under control of a programmed microprocessor. The microprocessor includes a memory for storing state information therein and is programmed to periodically compute an average heart rate value during a predetermined time interval, as well as any change in the heart rate following the incremental adjustment of the length of the A-V delay interval from a lower limit toward an upper limit, but only when the heart rate is determined to be stable and when variations in the heart rate are determined to be below a predetermined threshold. There is stored in the memory for each incremental adjustment of the A-V interval a corresponding steady state mean heart rate value. When the series of incremental adjustments in A-V interval length reaches an upper limit, the contents of the memory are read out and the particular A-V interval value corresponding to the lowest stored value of the mean heart rate is then used in controlling the operation of the variable frequency pulse generator. In this way, the body's own reaction in terms of a heart rate change to a change in the A-V interval of the stimulating device can be used to determine an optimum A-V delay interval for that patient and no extra sensor of any type is required.

DESCRIPTION OF THE DRAWINGS

The foregoing features and advantages of the invention will become more apparent to those skilled in the art from the following detailed description of the preferred embodiment, especially when considered in conjunction with the accompanying drawings in which.

DESCRIPTION OF THE PREFERRED EMBODIMENT

Figure 1:
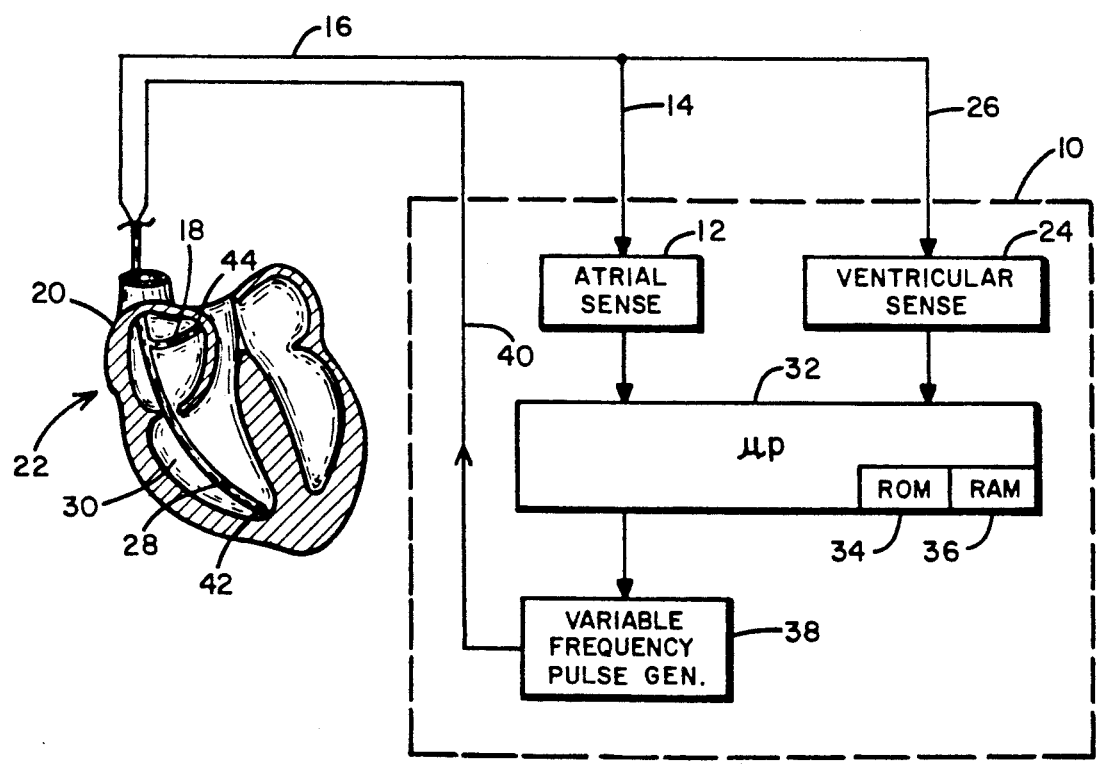
FIG. 1 is a block diagram of the cardiac rhythm management device in accordance with the present invention.

Referring first to the block diagram of FIG. 1, there is shown enclosed by the broken line box 10 the cardiac rhythm management device constructed in accordance with the present invention. It is seen to include an atrial sense amplifier 12 which is coupled by a conductor 14 in a pacing lead 16 to an atrial sense electrode 18 positioned within the right atrium 20 of the heart 22. In a similar fashion, a ventricular sense amplifier 24 is included in the cardiac rhythm management device 10 and is connected by a conductor 26 in the lead 16 to a sensing electrode 28 positioned in the right ventricular chamber 30.

The outputs from the atrial sense amplifier 12 and the ventricular sense amplifier 24 are connected as inputs to a microprocessor-based controller 32. Operatively coupled to the microprocessor-based controller 32 is a ROM memory 34 and a RAM memory 36. As is conventional, the ROM memory 34 is arranged to store a program of instructions executable by the microprocessor 32. The RAM memory 36 is provided to store state variables and operands, all as will be further described hereinbelow.

The controller 32 is connected in a controlling relationship to a variable frequency pulse generator 38 whose output is applied over a conductor 40 in the lead 16 to a cardiac stimulating electrode 42, typically located near the apex of the right ventricle. While not necessary to the device of the present invention, the variable frequency pulse generator 38 may also be connected by a separate lead (not shown) to an atrial stimulating electrode 44.

The sensing electrode 28 picks up ventricular depolarization signals and feeds them over the lead 16 and the conductor 26 to the ventricular sense amplifier. In that the output of this sense amplifier is made available to the microprocessor in the controller 32, the microprocessor can readily be programmed to compute a R-to-R interval from which heart rate can be determined, all as is well known in the art. Furthermore, the microprocessor-based controller 32 is capable of receiving atrial depolarization signals, via the atrial sense amplifier 12, and then issuing a command to the variable frequency pulse generator 38 to deliver a stimulating pulse to the electrode 42 a predetermined A-V delay interval following the occurrence of an atrial event signal.

With the foregoing understanding of the circuit components in mind, consideration will next be given to the algorithm defining the program of instructions typically stored in the ROM memory 34 of the microprocessor-based controller 32 which allows for the optimization of the A-V interval or some other related pacing parameter to yield optimal cardiac function, but which does not require an additional apparatus for sensing some cardiac function.

Assuming that the cardiac rhythm management device 10 in FIG. 1 is operating in the VDD pacing mode, at predetermined intervals during the course of a day, the microprocessor 32 is programmed to be activated to monitor the patient's heart rate and heart rate variability. These operations are identified by block 50 in the software flow diagram of FIG. 2. With no limitation intended, the heart rate variability may be computed as a standard deviation of the heart rate. The decision block 52 shows that heart rate and heart rate variability are compared to thresholds and if either exceeds its corresponding threshold, control loops back over path 54 and the monitoring step 50 continues until such time as the heart rate and heart rate variability have fallen below their established threshold values. The threshold values may be either preprogrammed or operationally determined and set at a level where it can be assumed that the patient is at rest or sleeping. When this condition prevails, the pacemaker enters the parameter adjustment loop, via path 56 in FIG. 2.

When in the adjustment loop, the A-V interval of the pacemaker is first set to a programmed-in minimum value and then this value is slowly incremented in discrete steps and at predetermined times until a maximum A-V value is reached. More particularly, the operation designated by block 58 calls for the A-V interval to be set at a minimum value, such as 0 milliseconds. The microprocessor continues to sample the patient's R-wave activity and to compute heart rate and heart rate variability (block 60), but only when the mean heart rate is approximately constant (block 62) and when the heart rate variability is less than the program threshold (block 64) will the computed mean heart rate for the then current A-V interval be stored in the RAM memory 36 (block 66). A test is then made to determine whether the A-V interval has been advanced up to a preset maximum. If the A-V interval is less than the maximum (decision block 68), the A-V interval will be incremented by a small time value, e.g., 25–50 milliseconds (block 70) and control then loops back, via path 72, to the operation set out in block 60. After several iterations of the step comprising the parameter adjustment loop, the test at block 68 will reveal that the current A-V interval has reached the preset maximum allowed for it. The contents of the RAM memory will then be read out and a determination made as to the length of the A-V interval that corresponds to the lowest mean heart rate which had been sampled. Then, as indicated by block 74, the pacemaker's A-V interval is set to the value that corresponds to the minimum mean heart rate.

It can be seen, then, that during the parameter adjustment sequence, at each interval, the mean heart rate is monitored until it reaches a new steady-state value and then the variability of the heart rate measurements is monitored to guarantee that the patient is still in a stable state. Once the steady-state value is reached, a new mean value for heart rate is collected over a time period of one to two minutes, with the value being recorded in the RAM memory of the microprocessor.

The rate threshold and the variability threshold used in the above parameter adjustment sequence may be preprogrammed by the physician based upon patient information which the physician has gathered in advance. It is also possible to experimentally determine the threshold values which would then be set by the device 10 itself. For example, by monitoring the maximum and minimum heart rates during a day or by generating a histogram of heart rates, the heart rate threshold can be set at a value that is a predetermined number of beats-per-minute above the minimum heart rate and the variability threshold can be set at a percentage of the difference between maximum and minimum heart rates and/or the variability of the heart rate.

Figure 2:
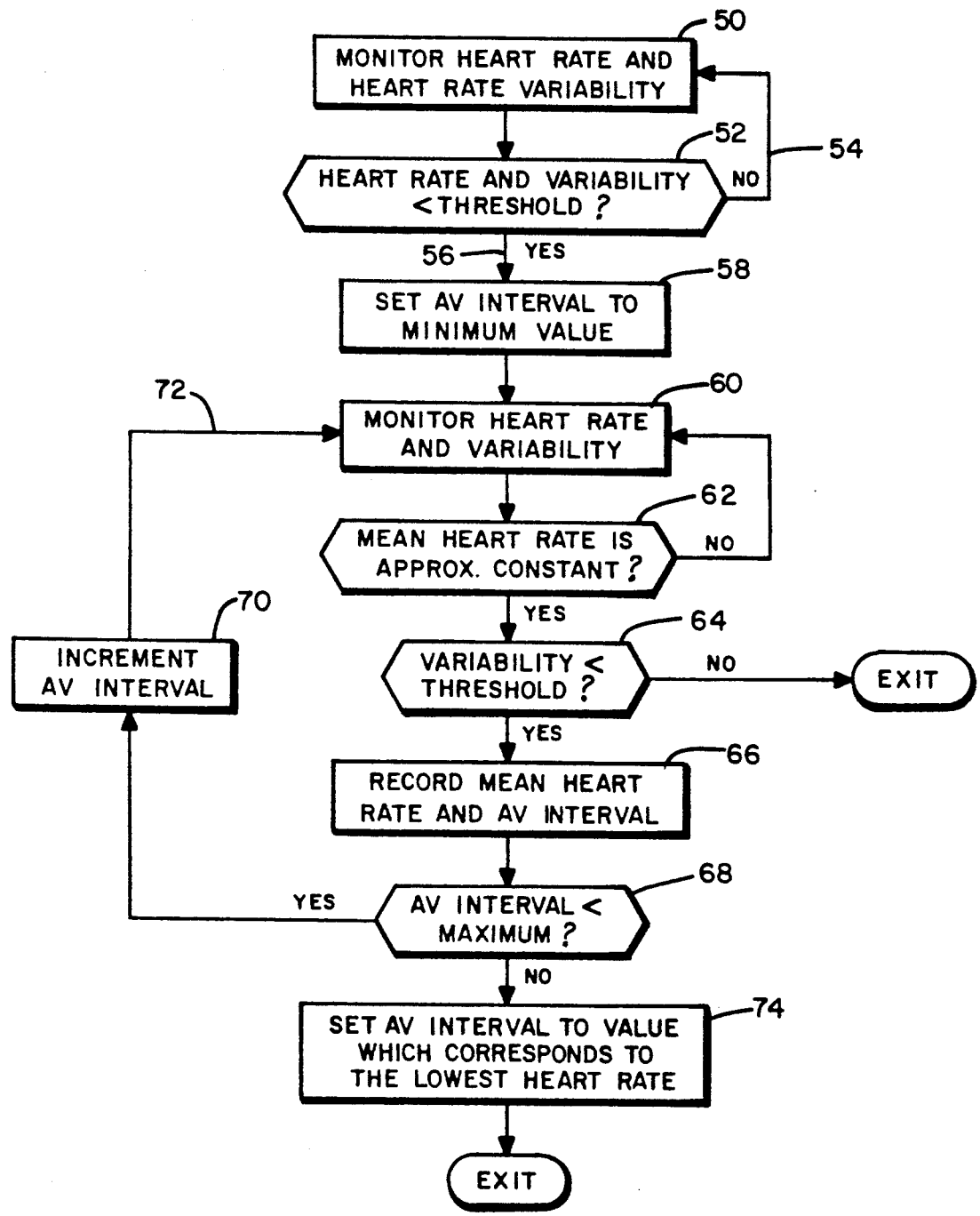
FIG. 2 is a flow diagram illustrating the algorithm comprising the software executed by the microprocessor in implementing the present invention.

This invention has been described herein in considerable detail in order to comply with the Patent Statutes and to provide those skilled in the art with the information needed to apply the novel principles and to construct and use such specialized components as are required. The flow chart of FIG. 2 is sufficient to allow a person skilled in the computer programming arts to develop the necessary sequence of instructions (program) for carrying out the depicted algorithm. It is to be understood that the invention can be carried out by specifically different equipment and devices, and that various modifications, both as to the equipment details and operating procedures, can be accomplished without departing from the scope of the invention itself.

What is claimed is:

1. A cardiac pacemaker comprising;
   (a) means for sensing atrial and ventricular depolarization signals;
   (b) a variable frequency pulse generator having a control input and an output;
   (c) means for coupling said output to at least one ventricle;
   (d) control means coupled to said control input of said variable frequency pulse generator and to said means for sensing atrial and ventricular depolarization signals, said control means including a microprocessor having a memory for storing state information therein, said microprocessor being programmed to periodically compute heart rate and variations in said heart rate and incrementally adjust an A-V delay interval between the sensing of an atrial depolarization signal and a next ensuing output from said variable frequency pulse generator from a lower limit toward an upper limit only when said heart rate is determined to be stable and variations in said heart rate are determined to be below a predetermined threshold and to store for each incremental adjustment of A-V interval that A-V interval and a corresponding steady state mean heart rate value; and means responsive to said A-V interval reaching said upper limit for reading out from said memory the state information consisting of the stored A-V interval value corresponding to the lowest stored value of mean heart rate, said control means then using that A-V interval value in controlling operation of said variable frequency pulse generator.

2. The cardiac pacemaker as in claim 1 wherein said predetermined threshold is a programmable parameter.

3. The cardiac pacemaker as in claim 1 wherein said predetermined threshold for heart rate is set by said microprocessor to a value which is greater than the lowest mean heart rate value stored in said memory during a preceding time interval.

4. The cardiac pacemaker as in claim 3 wherein said predetermined threshold for variations in heart rate is a predetermined percentage of the difference between maximum and minimum mean heart rate values stored in said memory during a preceding time interval.

5. The cardiac pacemaker as in either of claims 3 or 4 wherein said preceding time interval is in a range of from 12 hours to 24 hours.

6. A method of operating a cardiac pacemaker, said pacemaker being of a dual chamber type having means for sensing atrial and ventricular depolarization signals and pulse generator means for applying stimulating pulses to at least one ventricle following a predetermined A-V interval from an occurrence of a preceding atrial depolarization signal and a microprocessor-based controller having a memory means for storing state variables therein, said controller being coupled to said sensing means and in controlling relation to said pulse generator means, comprising the steps of;
   (a) monitoring heart rate and heart rate variability;
   (b) setting the A-V interval to a minimum value when the monitored heart rate and heart rate variability are each below associated threshold values;
   (c) continuing to monitor heart rate and variability following step (b) so long as the heart rate and heart rate variability remain below said threshold value until the heart rate reaches a steady state value;
   (d) storing a mean heart rate value and associated A-V delay value in said memory means;
   (e) incrementing said A-V interval from said minimum value and repeating steps (c) and (d) until the A-V interval reaches a predetermined maximum value;
   (f) reading from said memory means the A-V interval associated with said minimum mean heart rate; and
   (g) using the A-V interval read out from said memory for controlling said pulse generator means.

* * * * *